United States Patent [19]

Pujado

[11] 4,262,151
[45] Apr. 14, 1981

[54] PROCESS FOR THE RECOVERY OF PHENOL FROM A REACTION MIXTURE RESULTING FROM THE ACID CLEAVAGE OF CUMENE HYDROPEROXIDE

[75] Inventor: Peter R. Pujado, Palatine, Ill.
[73] Assignee: UOP Inc., Des Plaines, Ill.
[21] Appl. No.: 108,750
[22] Filed: Dec. 31, 1979
[51] Int. Cl.³ .................. C07C 37/68; C07C 37/86
[52] U.S. Cl. .................................................. 568/754
[58] Field of Search .................................... 568/754

[56] References Cited
U.S. PATENT DOCUMENTS 3,931,339  1/1976  Cooke ............................ 568/754
4,016,213  4/1977  Cheun et al. ..................... 568/754

*Primary Examiner*—Werren B. Lone
*Attorney, Agent, or Firm*—James R. Hoatson, Jr.; Robert W. Welch; William H. Page, II

[57] ABSTRACT

A process for the recovery of phenol from a reaction mixture resulting from the acid cleavage of cumene hydroperoxide is disclosed. Neutralization of the acidic reaction mixture is effected with sodium phenate—a product derived from the subsequent recovery of phenol and recycled to the neutralization process. The resulting mixture is further treated to effect an improved separation of the salt of neutralization therefrom.

6 Claims, 1 Drawing Figure

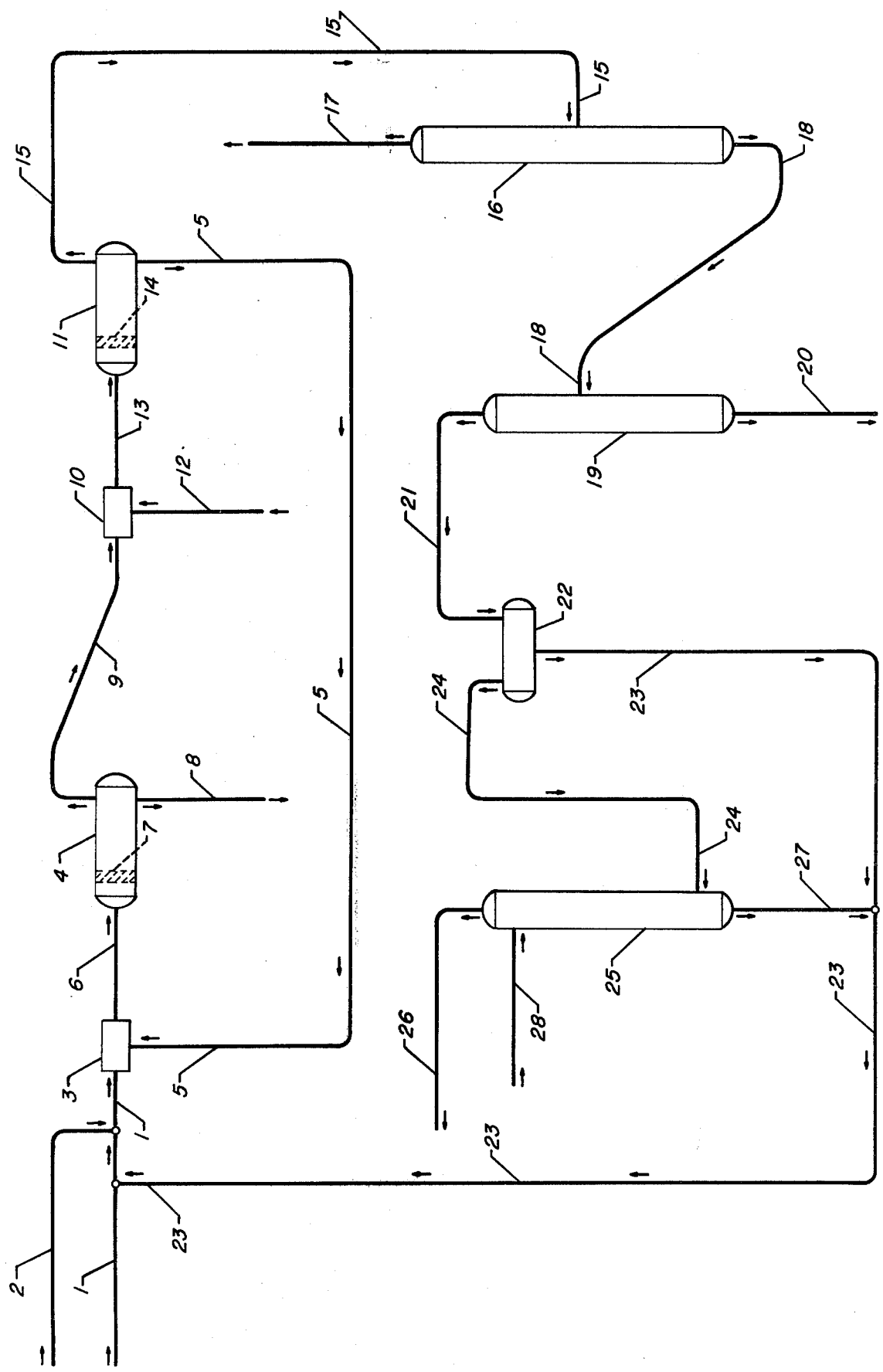

PROCESS FOR THE RECOVERY OF PHENOL FROM A REACTION MIXTURE RESULTING FROM THE ACID CLEAVAGE OF CUMENE HYDROPEROXIDE

This invention relates to a process for the recovery of a phenol from a reaction mixture resulting from the acid cleavage of an alpha hydroperoxy derivative of an alkyl-substituted aromatic compound, and, in particular, to a process for the recovery of phenol from a reaction mixture resulting from the acid cleavage of cumene hydroperoxide.

In general, phenols are prepared by the oxidation of an alkyl-substituted aromatic hydrocarbon and the subsequent acid cleavage of the resulting alpha hydroperoxy derivative thereof to form a reaction mixture comprising a phenol, a ketone and unreacted alkyl-substituted aromatic hydrocarbon. The acid cleavage is generally effected in the presence of an aqueous acid catalyst, usually 50–98% sulfuric acid in aqueous solution, and preferably at least 70%, or in the presence of an aqueous hydrochloric or perchloric acid solution. The present invention is particularly directed to a process wherein phenol is prepared by the air oxidation of cumene and the subsequent sulfuric acid cleavage of the resulting cumene hydroperoxide to form a reaction mixture comprising phenol, acetone and unreacted cumene. In addition to the principal products, there are formed varying amounts of by-products such as mesityl oxide, alpha-methylstyrene, p-cumylphenol, phenyldimethylcarbinol, acetophenone, and higher molecular weight phenols.

In the process of recovering phenol from the acid cleavage reaction mixture, the acidic reaction mixture is initially neutralized, either directly by the addition of caustic, or indirectly by contact with an ion exchange resin. In any case, the neutralized reaction mixture is fed to a distillation column, commonly referred to as a crude acetone column, at conditions to effect a crude separation of those materials boiling below phenol whereby an overhead fraction is recovered comprising substantially all of the acetone and lower boiling by-products, as well as a substantial portion of the water and unreacted cumene. Acetone is subsequently recovered, as is cumene, by the further distillation of the crude acetone column overhead, the cumene being recycled to the oxidation process.

The bottoms fraction recovered from the crude acetone column, comprising phenol and alpha-methylstyrene as well as the balance of the water and unreacted cumene, is typically treated for the separation of heavy ends and thereafter fed to a distillation column, commonly referred to as a cumene or alpha-methylstyrene column. The last-mentioned column is operated at conditions to separate an overhead fraction comprising water, cumene and alpha-methylstyrene from the higher boiling phenol product. The phenol, recovered as the bottoms fraction, further contains certain impurities, e.g., mesityl oxide, hydroxy acetone, etc., and said impurities are treated and separated from said bottoms fraction to yield a substantially pure phenol product.

The overhead fraction from the cumene column will invariably comprise a significant amount of phenol as well as cumene and alpha-methylstyrene. It has heretofore been the practice to caustic-extract this overhead fraction, and the cumene/alpha-methylstyrene recovered as a water-immiscible organic phase is either fractionated for alpha-methylstyrene recovery or hydrotreated and recycled to oxidation as cumene. The phenol is recovered as sodium phenate in the aqueous phase, a practice which has heretofore necessitated a separate phenol recovery facility wherein the aqueous sodium phenate solution is acid treated, the resulting phenol being recycled and combined with the acid cleavage product for recovery as heretofore described, and the acidifying agent being subsequently caustic-treated for safe disposal.

In one of its broad aspects, the present invention embodies a process for the direct neutralization of a reaction mixture resulting from the acid cleavage of an alpha hydroperoxy derivative of an alkyl-substituted aromatic hydrocarbon which comprises the steps of (a) effecting the direct neutralization of said acid cleavage reaction mixture and forming a reaction mixture comprising a phenol, a ketone, a secondary alkylbenzene and a salt of neutralization; (b) charging the salt-containing reaction mixture to the mixing stage of the first of a plurality of mixer-settler means, and admixing the same therein with a salt-containing aqueous phase charged to said mixing stage in accordance with step (g); (c) separating an organic phase and an aqueous phase in the settling stage of said first mixer-settler means; (d) charging said organic phase to the mixing stage of each succeeding mixer-settler means from the settling stage of the next preceding mixer-settler means and effecting a progressive decrease in the salt concentration of said organic phase in contact with an aqueous phase charged to said mixing stage in accordance with step (g); (e) charging a substantially salt-free water stream to the mixing stage of the last of said plurality of mixer-settler means, and admixing the same therein with an organic phase charged to said mixing stage in accordance with step (d); (f) separating an organic phase and an aqueous phase in the settling stage of said last mixer-settler means; (g) charging said aqueous phase to the mixing stage of each preceding mixer-settler means from the settling steps of the next succeeding mixer-settler means, and effecting a progressive increase in the salt concentration of said aqueous phase in contact with an organic phase charged to said mixing stage in accordance with step (d); (h) discharging the salt-containing aqueous phase from the settling stage of said first mixer-settler means substantially free of said organic phase; and (i) recovering a substantially salt-free organic phase comprising a phenol, a ketone and unreacted alkyl-substituted aromatic hydrocarbon from the settling stage of said last mixer-settler means.

One of the more specific embodiments of this invention concerns a process for the direct neutralization of a reaction mixture resulting from the sulfuric acid cleavage of cumene hydroperoxide which comprises the steps of (a) contacting the cleavage reaction mixture with sodium phenate and forming a neutralized reaction mixture comprising phenol, acetone, cumene and a sodium sulfate salt of neutralization; (b) charging the sodium sulfate-containing reaction mixture to the mixing stage of a first mixer-settler means and admixing the same therein at a temperature of from about 95° to about 120° F. and at a pH of from about 2 to about 4 with a sodium sulfate-containing aqueous phase charged to mixing stage in accordance with step (g); (c) separating an organic phase and an aqueous phase in the settling stage of said first mixer-settler means at said conditions of temperature and pH; (d) charging the organic phase from the settling stage of said first mixer-settler means to the mixing stage of a second mixer-settler means and effecting a progressive decrease in the sodium sulfate concentration of said organic phase at a temperature of from about 95° to about 120° F. and at a pH of from about 2 to about 4 in contact with an aqueous phase charged to said mixing stage in accordance with step (e); (e) charging a substantially salt-free water stream to the mixing stage of said second mixer-settler means and admixing the same therein with the organic phase charged to said mixing stage in accordance with step (d); (f) separating an organic phase and an aqueous phase in the settling stage of said second mixer-settler means at said conditions of temperature and pH; (g) charging said aqueous phase from the settling stage of said second mixer-settler means to the mixing stage of said first mixer-settler means and effecting a progressive increase in the salt concentration of said aqueous phase in contact with said cleavage reaction mixture charged to said mixing stage in accordance with step (b); (h) discharging the resulting sodium sulfate-containing aqueous phase from the settling stage of said first mixer-settler means substantially free of said organic phase; and (i) recovering an organic phase comprising phenol, acetone and cumene from the settling stage of said second mixer-settler means substantially free of sodium sulfate.

The overall process to which this invention pertains concerns the oxidation of an alkyl-substituted aromatic hydrocarbon, and the alpha hydroxy derivatives thereof may be represented by the general formula

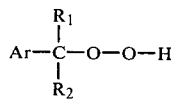

wherein Ar represents an aromatic hydrocarbon radical which may be an aryl radical or an alkaryl radical, and the hydroperoxy group (—O—O—H) is attached to a carbon atom alpha the aromatic nucleus, and R, and $R_2$ may be hydrogen or the same or different alkyl, cycloalkyl, aryl, aralkyl or alkaryl hydrocarbon radicals, or $R_1$ and $R_2$ together with the said alpha carbon atom to which they are attached may form a cycloalkyl group containing up to about 8 carbon atoms, for example, as in the case of 1-phenyl-1-hydroperoxy-cyclohexane. $R_1$ and $R_2$ are preferably n-alkyl hydrocarbon radicals so that the hydroperoxide is an alpha hydroperoxy derivative of a secondary alkylbenzene. The alpha hydroperoxy derivatives of alkyl substituted aromatic hydrocarbons herein contemplated thus include benzyl hydroperoxide,
alpha-methylbenzyl hydroperoxide,
alpha-methyl-p-methylbenzyl hydroperoxide,
alpha,alpha-dimethylbenzyl hydroperoxide (cumene hydroperoxide),
alpha,alpha-dimethyl-p-methylbenzyl hydroperoxide,
alpha,alpha-dimethyl-p-ethylbenzyl hydroperoxide,
   alpha,alpha,alpha,alpha'-tetramethyl-p-xylyl dihydroperoxide,
alpha-methyl-alpha-phenylbenzyl hydroperoxide,
alpha-alpha-dimethylnaphthylmethyl hydroperoxide,
1,phenylcyclohexyl hydroperoxide, and the like. The present invention is particularly directed to a process for the recovery of phenol from a reaction mixture resulting from the acid cleavage of alpha,alpha-dimethylbenzyl hydroperoxide, or isopropylbenzene hydroperoxide, more commonly referred to as cumene hydroperoxide.

The aforesaid oxidation reaction is effected at conditions well known in the art. The hydroperoxide oxidation product can be prepared by direct liquid phase oxidation of the selected alkyl-substituted aromatic hydrocarbon with oxygen, or an oxygen-containing gas such as air, usually at an elevated temperature. The oxidation reaction proceeds slowly through an initial induction period, accelerating to a more favorable rate with the formation of the hydroperoxide which exerts a catalytic effect on the oxidation reaction. This initial induction period is eliminated, or substantially reduced, by initially including a hydroperoxide in the reaction mixture, usually the hydroperoxide product of the reaction. However, other materials are disclosed in the art which exhibit a similar catalytic effect. Temperatures effecting the oxidation reaction range from about room temperature to about the boiling point of the hydrocarbon subjected to oxidation, which, in the case of cumene, is about 305° F. In general, it is preferred to utilize an elevated temperature in the range of from about 120° to about 265° F. The optimum temperature will depend on the particular alkyl-substituted aromatic hydrocarbon to be oxidized and on the reaction conditions otherwise employed. The oxidation can be effected at pressures ranging from about atmospheric to about 500 psig., although a pressure not exceeding about 90 psig. is generally preferred. It is desirable to limit the contact time of the reactants at oxidation conditions to effect substantially less than complete conversion of the alkyl-substituted aromatic hydrocarbon to the corresponding hydroperoxide. For example, in the oxidation of cumene, it is desirable to limit the contact time of the cumene and the oxidizing agent so that the concentration of the resulting cumene hydroperoxide does not exceed about 30 wt.%.

The further description of the process of this invention is presented with reference to the attached drawing. The drawing is a simplified flow diagram of a phenol recovery process representing one preferred embodiment of this invention and is not intended as an undue limitation on the generally broad scope of the invention as set out in the appended claims. Certain hardware such as valves, pumps, compressors, heat exchangers, instrumentation and controls, have been omitted as not essential to a clear understanding of the invention, the use and application of said hardware being well within the skill of the art.

Referring then to the drawing, a reaction mixture resulting from the acid cleavage of cumene hydroperoxide is charged to the phenol recovery process through line 1. In this instance, the cleavage reaction mixture comprises, on an hourly basis, about 115.8 moles of phenol, 123.8 moles of acetone, 37.9 moles of unreacted cumene, 4.8 moles of alpha-methylstyrene, 0.3 moles of sulfuric acid, and 29.9 moles of water. A recycle stream from line 21, originating as hereinafter described and comprising about 3.4 moles of sodium phenate and 0.5 moles of sodium hydroxide, is combined with the acid cleavage reaction mixture in line 1 whereby said reaction mixture is neutralized and said sodium phenate is recovered therein as phenol. Said recycle stream further comprises about 0.3 moles of acetone and 87.2 moles of water discharged into line 1 per hour. In this instance, about 1.6 moles of 98 wt.% sulfuric acid are metered through line 2 per hour to adjust the pH of the combined streams to a pH of about 6 or less and facilitate the subsequent separation of phenol therefrom.

The resulting mixture is then continued through line 1 to the mixing stage 3 of a first mixer-settler means comprising said mixing stage 3 and a settling stage 4, said mixer-settler means being hereinafter referred to as mixer-settler means 3–4. In said mixing stage, said mixture is further admixed with a sodium sulfate-containing aqueous stream charged thereto from line 5 and originating as hereinafter described. The effluent from the mixing stage 3 is transferred through line 6 to the settling stage 4, and processed through a coalescing means 7 to promote the separation of the organic and aqueous phases therein. The organic and aqueous phases are preferably treated in the mixer-settler means at a temperature in excess of about 90° F., and more preferably at a temperature of from about 95° to about 120° F. This allows for a maximum concentration of sodium sulfate in the aqueous phase, taking full advantage of the salting-out effect of the sodium sulfate. Further, any sodium sulfate precipitating from the aqueous phase will do so as a free-flowing anhydrous form less apt to deposit and accumulate on a surface and cause a fouling of process equipment.

Substantially all of the phenol is recovered in the organic phase, a result which is largely attributable to the salt-out effect of the sodium sulfate recovered in the aqueous phase. The sodium sulfate-containing aqueous phase that settles out is discharged through line 8, about 1.9 moles of sodium sulfate in 61.2 moles of water being discharged from the recovery process in this manner. The upper organic phase is withdrawn from the settling stage 4 by way of an overhead line 9 and transferred to the mixing stage 10 of a second mixer-settler means comprising said mixing stage 10 and a settling stage 11, said second mixer-settler means being hereinafter referred to as mixer-settler means 10–11. In the mixing stage 10, the organic phase from line 9 is admixed with a substantially salt-free aqueous phase introduced to said mixing stage 10 at a rate of about 25.3 moles per hour by way of line 12. The resulting mixed phases are then transferred through line 13 to the settling stage 11 of the mixer-settler means 10–11. The mixture is processed through a coalescing means 14 in the settling stage 11 to facilitate separation of the organic and aqueous phases therein. Essentially all of the sodium sulfate remaining in the organic phase is recovered in the aqueous phase. The aqueous phase is then withdrawn from the settling stage 11 by way of line 5 and transferred to the mixing stage 3 of the first mixer-settler means 3–4 to provide about 61.7 moles of water per hour to said mixing stage.

It is contemplated that, by reason of a lower sodium sulfate concentration in the aqueous phase of the second mixer-settler means 10–11, some organics, particularly phenol and acetone, will be contained in the aqueous phase withdrawn from the settling stage 11. However, by reason of the higher sodium sulfate concentration which occurs in the first mixer-settler means 3–4, said organics will be sprung from the aqueous phase transferred thereto and recovered in the organic phase in the settling stage 4, and ultimately recovered from the settling stage 11 through line 15.

About 119.2 moles of phenol, 124.1 moles of acetone, 37.9 moles of cumene, 4.8 moles of alpha-methylstyrene and 85.2 moles of water are recovered from the settling stage 11 through the overhead line 15 on an hourly basis, and this mixture is charged to a crude acetone column 16.

About 123.8 moles of acetone per hour are distilled overhead from the crude acetone column in admixture with about 9.2 moles of cumene and 46.8 moles of water per hour. This mixture, representing the bulk of the acetone produced, is taken overhead through line 17 and further treated in distillation means, not shown, for the recovery of a substantially pure acetone product—the cumene being recycled to the oxidation phase of the overall process.

A bottoms fraction, withdrawn from the crude acetone column 16 by way of line 18, is charged to a cumene column 19, said bottoms fraction comprising about 119.2 moles of phenol, 0.3 moles of acetone, 28.7 moles of cumene, 4.8 moles of alpha-methylstyrene and 38.4 moles of water on an hourly basis. About 115.8 moles of phenol are recovered per hour from the bottom of the cumene column 19 by way of line 20, and this product is further treated in distillation means, not shown, for the recovery of a substantially pure phenol product.

The overhead fraction, withdrawn from the cumene column 19 by way of line 21, comprises about 3.3 moles of phenol, 0.3 moles of acetone, 28.7 moles of cumene, 4.8 moles of alpha-methylstyrene and 38.4 moles of water per hour, and this fraction is charged to a settler 22. The aqueous phase which settles out comprises substantially all of the water charged to the settler, and this water is withdrawn through line 23 at a rate of about 38.4 moles per hour along with about 0.2 moles of phenol and 0.1 moles of acetone per hour. This material is ultimately recycled to the phenol recovery process as hereinafter described.

Substantially all of the cumene charged to the settler 22 is recovered in the organic phase which forms therein, and this cumene is ultimately recycled to the oxidation phase of the overall process. The organic phase will also comprise acetone, a substantial amount of phenol, and substantially all the alpha-methylstyrene charged to said settler 22. The phenol adversely affects the oxidation phase of the overall process, is well known. Therefore, in keeping with the prior art practice, the organic phase is caustic-treated whereby the phenol is converted to sodium phenate and recovered with the acetone in the resulting aqueous phase.

Referring then to the drawing, the organic phase is recovered from the settler 22 through an overhead line 24 and transferred to the bottom of a caustic wash column 25. Said organic phase provides about 3.2 moles of phenol, 0.2 moles of acetone, 28.7 moles of cumene and 4.8 moles of alpha-methylstyrene to the caustic wash column per hour. An aqueous caustic stream charged to the upper portion of the caustic wash column through line 28 provides about 48.8 moles of water and 3.9 moles of sodium hydroxide thereto per hour. The organic phase passes upwardly in countercurrent contact with the aqueous caustic phase and, in the process, phenol is recovered in the aqueous caustic phase as sodium phenate. Essentially all of the cumene and alpha-methylstyrene is recovered from the caustic wash column 25 through an overhead line 26 at the rate of about 28.7 moles of cumene and 4.8 moles of alpha-methylstyrene per hour. This stream is typically hydrotreated to convert the alpha-methylstyrene portion to cumene, and the hydrotreated stream is then recycled to the oxidation phase of the overall process. Alternatively, this alpha-methylstyrene can be recovered as a by-product by conventional distillation means and the remaining cumene is recycled to the oxidation reactor.

It has heretofore been the general practice to provide one or more suitable vessels wherein the aqueous caustic phase, such as is recovered from the caustic wash column 25, is acid-treated and the sodium phenate contained therein is hydrolyzed and subsequently recovered as phenol. Pursuant to the process of this invention, said aqueous phase is recycled and combined with the acid cleavage reaction mixture in line 1. It will be appreciated that utilization of this internal recycle stream in this manner will not only afford a reduced inventory of acid and caustic in the phenol recovery scheme, but also the elimination of one or more vessels. Accordingly, the aqueous caustic phase recovered from the bottom of the caustic wash column 25 through line 27 is combined with the aforementioned material recovered from the settler 22 through line 23, and the combined streams are continued through line 23 to be admixed with the acid cleavage reaction mixture in line 1 as heretofore described. It will be further appreciated that by operation of the neutralization and settler/separation vessels 3, 4, 10 and 11 at a temperature above 90° F., and preferably between 95° and 120° F., it is possible to minimize the water requirements in the neutralization stage thus decreasing the load on the effluent treatment section and, in addition, minimizing the flow of phenol and acetone to effluent treatment on account of the salting-out effect accomplished by the higher saline concentration. Another benefit resulting from the operation at these temperatures is that any sodium sulfate that might accidentally crystallize out of the solution will do so as free flowing anhydrous sodium sulfate whereas, should the neutralization have been carried out at lower temperatures, the precipitate would have been in the form of sodium sulfate decahydrate which has a strong tendency to deposit on the walls as large crystalline needles and thus foul up the equipment.

The mixer-settler means herein contemplated will comprise a mixing stage and a settling stage. The mixing stage of the operation may be effected in a vessel separate from the settling stage, or the mixing and settling stages may be effected in a common vessel. The settling stage will preferably include a coalescing means, e.g., glass wool, to facilitate separation of the dispersion recovered from the mixing stage. The mixer-settler means employed herein are well known to the art of liquid-liquid extraction. Suitable mixer-settler means will be apparent with reference to pp. 415–416, Mass Transfer Operations, Chemical Engineering Series, 2nd Ed., published by McGraw-Hill.

I claim as my invention:

1. A process for the direct neutralization of a reaction mixture resulting from the sulfuric acid cleavage of cumene hydroperoxide which comprises the steps of:
   (a) effecting the direct neutralization of said acid cleavage reaction mixture with an alkali metal phenate and forming a cleavage reaction mixture comprising phenol, acetone, cumene and an alkali metal sulfate salt of neutralization;
   (b) charging the salt-containing cleavage reaction mixture to the mixing stage of the first of a plurality of mixer-settler means, and admixing the same therein at a temperature of from about 95° to about 120° F. with a salt-containing aqueous phase charged to said mixing stage in accordance with step (g);
   (c) separating an organic phase and an aqueous phase in the settling stage of said first mixer-settler means;
   (d) charging said organic phase to the mixing stage of each succeeding mixer-settler means from the settling stage of the next preceding mixer-settler means and effecting a progressive decrease in the salt concentration of said organic phase at a temperature of from about 95° to about 120° F. and in contact with an aqueous phase charged to said mixing stage in accordance with step (g);
   (e) charging a substantially salt-free water stream to the mixing stage of the last of said plurality of mixer-settler means, and admixing the same therein with an organic phase charged to said mixing stage in accordance with step (d);
   (f) separating an organic phase and an aqueous phase in the settling stage of said last mixer-settler means;
   (g) charging said aqueous phase to the mixing stage of each preceding mixer-settler means from the settling stage of the next succeeding mixer-settler means, and effecting a progressive increase in the salt concentration of said aqueous phase in contact with an organic phase charged to said mixing stage in accordance with step (d);
   (h) discharging the salt-containing aqueous phase from the settling stage of said first mixer-settler means substantially free of said organic phase; and,
   (i) recovering a substantially salt-free organic phase comprising phenol, acetone and cumene from the settling stage of said last mixer-settler means.

2. The process of claim 1 further characterized with respect to step (a) in that said acid cleavage reaction mixture is neutralized in contact with sodium phenate.

3. The process of claim 1 further characterized in that said mixer-settler means are maintained at a pH of from about 2 to about 6.

4. The process of claim 1 further characterized in that said mixer-settler means are maintained at a pH of from about 2 to about 4.

5. The process of claim 1 further characterized in that said plurality of mixer-settler means comprises two mixer-settler means.

6. The process of claim 1 further characterized in that said plurality of mixer-settler means comprises three mixer-settler means.

* * * * *